(12) United States Patent
Overtoom

(10) Patent No.: US 10,376,683 B2
(45) Date of Patent: Aug. 13, 2019

(54) CATHETER SYSTEM FOR DELIVERY OF A URETERAL CATHETER

(71) Applicant: Overtoom Limited, Dublin (IE)

(72) Inventor: Timotheus Theodorus Cornelis Overtoom, Bilthoven (NL)

(73) Assignee: Overtoom Limited, Dublin (IE)

( * ) Notice: Subject to any disclaimer, the term of this patent is extended or adjusted under 35 U.S.C. 154(b) by 642 days.

(21) Appl. No.: 14/904,988

(22) PCT Filed: Jul. 17, 2014

(86) PCT No.: PCT/EP2014/065403
§ 371 (c)(1),
(2) Date: Jan. 14, 2016

(87) PCT Pub. No.: WO2015/007849
PCT Pub. Date: Jan. 22, 2015

(65) Prior Publication Data
US 2016/0151615 A1    Jun. 2, 2016

(30) Foreign Application Priority Data

Jul. 17, 2013  (NL) ..................................... 2011186

(51) Int. Cl.
*A61F 2/04*      (2013.01)
*A61M 25/00*     (2006.01)
(Continued)

(52) U.S. Cl.
CPC ............. *A61M 31/005* (2013.01); *A61F 2/04* (2013.01); *A61M 25/0026* (2013.01);
(Continued)

(58) Field of Classification Search
CPC . A61F 2/04; A61F 2002/048; A61M 25/0026; A61M 25/09; A61M 25/10;
(Continued)

(56) References Cited

U.S. PATENT DOCUMENTS 4,787,884 A * 11/1988 Goldberg .......... A61M 25/0102
                                                          600/434
4,913,683 A *  4/1990 Gregory ............. A61M 27/008
                                                          604/500
(Continued)

FOREIGN PATENT DOCUMENTS

EP          0365269 A1    4/1990
WO        99/08740 A1    2/1999
WO      2012/154946 A1  11/2012

*Primary Examiner* — Adam Marcetich
(74) *Attorney, Agent, or Firm* — Hoffmann & Baron, LLP

(57) ABSTRACT

A catheter system for delivery of a ureteral catheter in a ureter includes a ureteral catheter, a pusher catheter to deliver the ureteral catheter at a desired location, a connection device, to connect, in an assembled state a distal end of the pusher catheter to a proximal end of the ureteral catheter, where, in the assembled state, the catheter system is configured and to deliver, when desired, fluid contrast agent near a proximal end of the ureteral catheter. The catheter system is also configured to deliver, when desired, fluid contrast agent near a distal end of the ureteral catheter.

14 Claims, 3 Drawing Sheets

(51) Int. Cl.
*A61M 25/09* (2006.01)
*A61M 25/14* (2006.01)
*A61M 39/00* (2006.01)
*A61M 31/00* (2006.01)
*A61M 39/10* (2006.01)
*A61M 27/00* (2006.01)
*A61M 25/10* (2013.01)

(52) U.S. Cl.
CPC ............ *A61M 25/09* (2013.01); *A61M 25/10* (2013.01); *A61M 27/008* (2013.01); *A61M 39/105* (2013.01); *A61F 2002/048* (2013.01)

(58) Field of Classification Search
CPC .............. A61M 27/008; A61M 31/005; A61M 39/105; A61M 25/01; A61M 25/0102; A61M 2025/0175; A61M 25/0194; A61M 2210/1082; A61B 2017/12054; A61B 2017/12086; A61B 2017/12095
See application file for complete search history.

(56) References Cited

U.S. PATENT DOCUMENTS

| | | | |
|---|---|---|---|
| 4,931,037 A | 6/1990 | Wetterman | |
| 4,963,129 A * | 10/1990 | Rusch | A61M 27/008 604/170.01 |
| 5,116,309 A * | 5/1992 | Coll | A61F 2/04 604/170.03 |
| 5,221,253 A * | 6/1993 | Coll | A61F 2/04 604/170.03 |
| 6,066,113 A | 5/2000 | Overtoom | |
| 2002/0123739 A1* | 9/2002 | Haacke | A61M 39/10 604/544 |
| 2002/0188246 A1* | 12/2002 | Hayner | A61M 25/0017 604/48 |
| 2003/0144623 A1* | 7/2003 | Heath | A61M 25/0023 604/4.01 |
| 2007/0156117 A1* | 7/2007 | Adams | A61J 15/0015 604/533 |
| 2007/0179474 A1* | 8/2007 | Cahill | A61M 39/02 604/533 |
| 2007/0276466 A1 | 11/2007 | Lavelle et al. | |
| 2009/0048654 A1* | 2/2009 | Chmura | A61F 2/95 623/1.11 |
| 2009/0187254 A1* | 7/2009 | Deal | A61L 31/10 623/23.7 |
| 2010/0114325 A1* | 5/2010 | Yang | A61F 2/04 623/23.7 |
| 2011/0077622 A1* | 3/2011 | Weisman | A61F 2/95 604/544 |
| 2011/0319904 A1* | 12/2011 | Hollett | A61F 2/94 606/108 |
| 2012/0290100 A1* | 11/2012 | Li | A61M 27/008 623/23.66 |

* cited by examiner

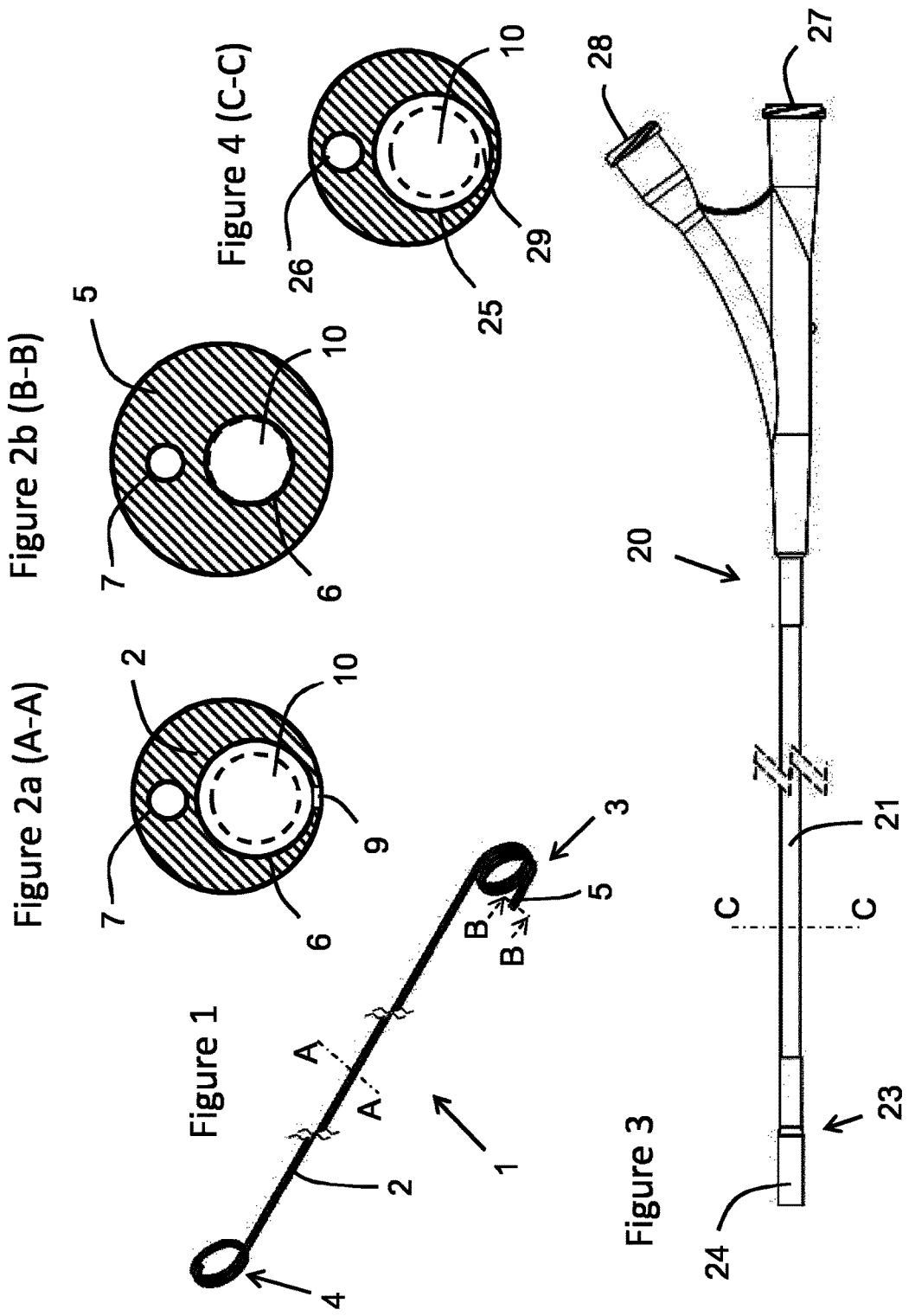

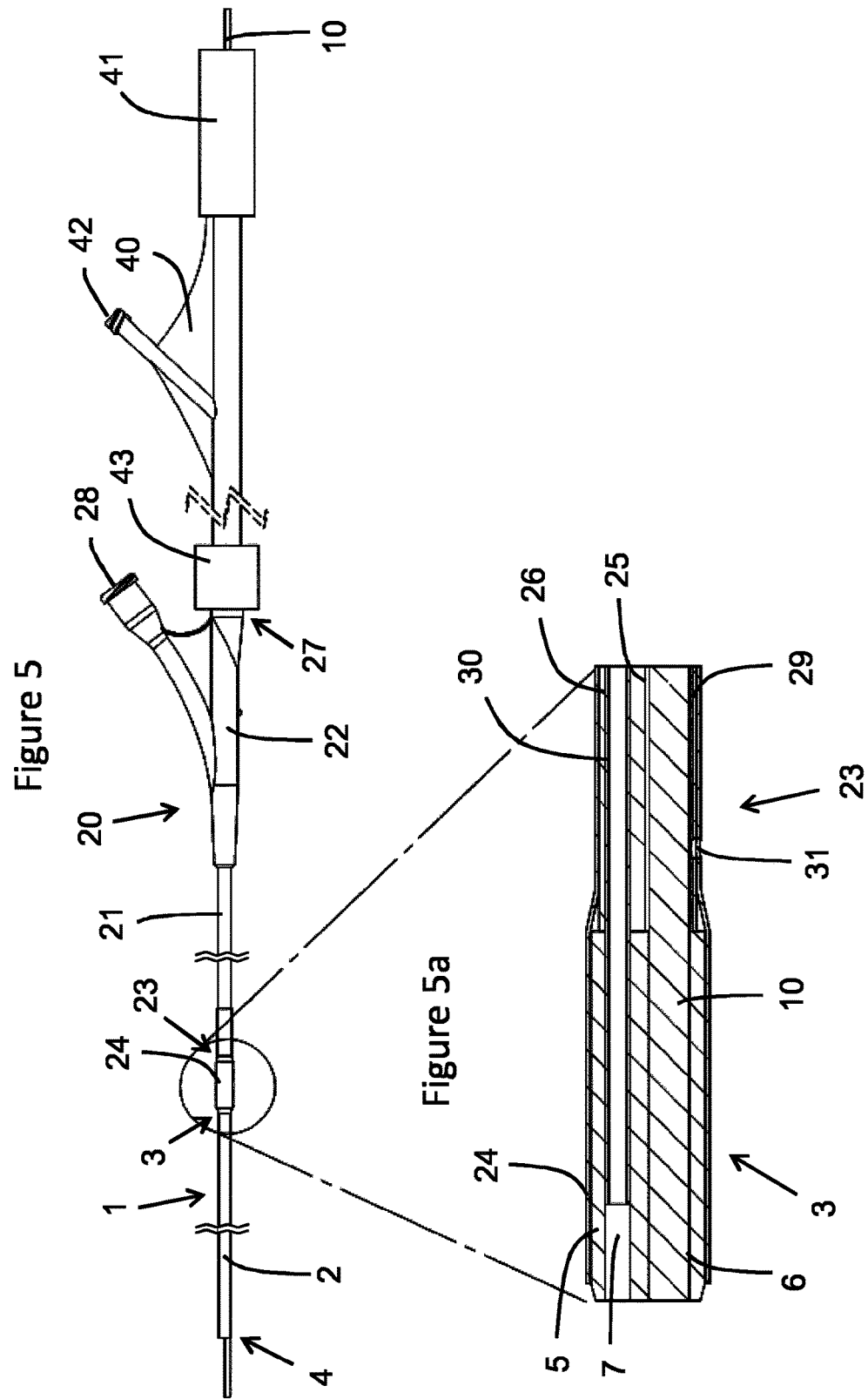

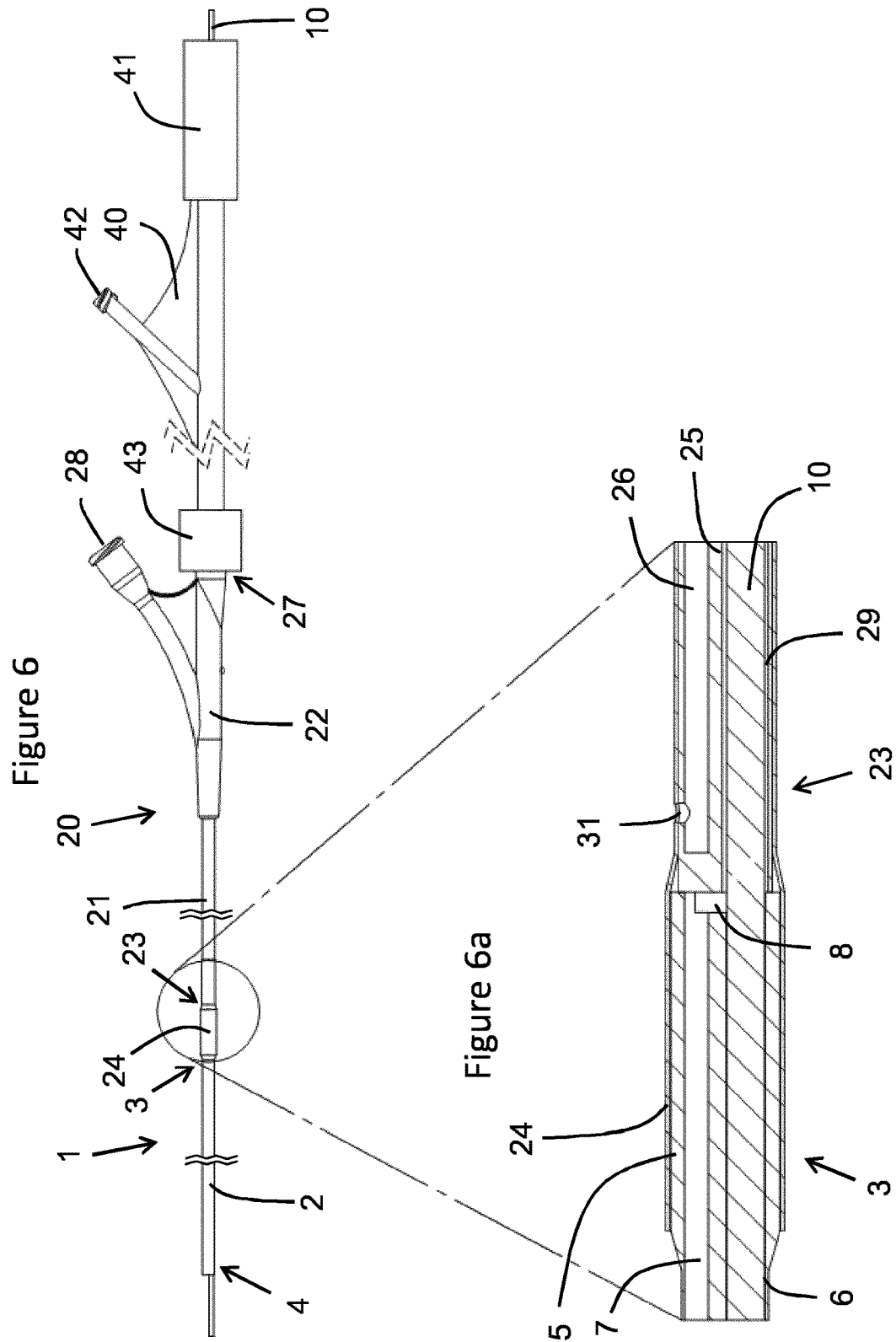

CATHETER SYSTEM FOR DELIVERY OF A URETERAL CATHETER

CROSS-REFERENCE TO RELATED APPLICATIONS

This application is the National Stage of International Application No. PCT/EP2014/065403 filed Jul. 17, 2014, which claims the benefit of Netherlands Application No. NL 2011186, filed Jul. 17, 2013, the contents of which is incorporated by reference herein.

FIELD OF THE INVENTION

The present invention relates to a catheter system for delivery of a ureteral catheter in a ureter for treatment of the ureter and/or the pyelo-ureter junction. The invention also relates to the use of a catheter system for the treatment of a diseased, in particular stenosed ureter of a patient, and a method for delivery of a ureteral catheter in a patient's ureter.

BACKGROUND OF THE INVENTION

Blockages in the ureter which are generally caused by constriction thereof, such as a stenosis and/or the presence of kidney stones, can lead to serious medical problems such as pain, inflammation of the ureter wall and prevention of urine drainage from the kidney. A ureteral catheter, sometimes also called ureteral or ureteric stent, is a thin tube inserted into the ureter to prevent or treat obstruction of the urine flow from the kidney and/or to ensure the patency of a ureter. The provision of a ureteral catheter may be a temporary provision, but a ureteral catheter may also placed in the ureter for longer periods. The length of the ureteral catheter used in adult patients may for example vary between 24 to 30 cm.

One or both ends of the ureteral catheter may be coiled to prevent it, after placement, from moving out of place. Such ureteral catheter is often referred to as a double J catheter or also JJ catheter or pig-tail catheter.

A ureteral catheter can be placed in the ureter cystoscopically or percutaneously. In the first method, the ureteral catheter is introduced into the ureter from the bladder towards the kidney of the patient. In a percutaneous placement method of the ureteral catheter, the ureteral catheter is inserted through an incision into the patient's body and brought into the kidney and subsequently through the ureter until a distal end of the catheter reaches a desired location in the bladder.

In both methods, accurate placement of the ureter catheter is important. In particular, the catheter ends in both the pyelum and bladder should be correctly placed to avoid tissue damage and/or discomfort to the patient.

SUMMARY OF THE INVENTION

It is an object of the invention to provide a catheter system for delivery of a ureteral catheter in a patient's ureter which provides improved accuracy and reliability in placement of the ureteral catheter in the patient's ureter, or at least to provide an alternative catheter system for delivery of a ureteral catheter in a ureter.

Another object of the invention may be to provide a catheter system to deliver a ureteral catheter in a ureter which may be suitable for both percutaneous insertion of the ureteral catheter from kidney towards bladder and cystoscopical delivery of the ureteral catheter from bladder towards kidney.

The invention provides a catheter system for delivery of a ureteral catheter in a ureter, in particular for treatment of the ureter and/or the pyelo-ureter junction, comprising:
- a ureteral catheter,
- a pusher catheter to deliver the ureteral catheter at a desired location,
- a connection device, to connect, in an assembled state, a distal end of the pusher catheter to a proximal end of the ureteral catheter, wherein, in the assembled state, the catheter system is configured to deliver, when desired, fluid contrast agent near a proximal end of the ureteral catheter.

The catheter system comprises a ureteral catheter to be placed in a patient's ureter, and a pusher catheter to advance the ureteral catheter by pushing towards the desired location in the ureter. In the assembled state, the pusher catheter and the ureteral catheter are connected to each other by a connection device.

This connection device may for example comprise a cover tube that can be arranged about the distal end of the pusher catheter and the proximal end of the ureteral catheter to hold these ends together.

The connection device may be an integral part of the pusher catheter or the ureteral catheter. For example, a cover tube may be fixed to a distal end of the pusher catheter to receive a proximal end of the ureteral catheter therein.

The catheter system may further comprise a guide wire over which the pusher catheter and the ureteral catheter can be moved towards the desired location.

It is remarked that the ureteral catheter may comprise a guide wire lumen extending from a proximal end of the ureteral catheter to a distal end of the ureteral catheter, and that the pusher catheter may comprise a second guide wire lumen extending from a proximal end of the pusher catheter to a distal end of the pusher catheter, which guide wire lumen and second guide wire lumen are aligned in the assembled state of the catheter system to receive a single guide wire over which the combination of the ureteral catheter and pusher catheter can be moved to a desired location. In some embodiments, the presence of the guide wire in the guide wire lumen and the second guide wire lumen, in particular in the transition region between the proximal end of the guide wire lumen and the distal end of the second guide wire lumen may be required to selectively deliver fluid contrast agent near a proximal end of the ureteral catheter.

In a catheter system according to the invention, the catheter system is configured to deliver, when desired, a fluid contrast agent near a proximal end of the ureteral catheter. By delivery of contrast fluid agent near the proximal end of the ureteral catheter the visibility of the ureteral catheter during insertion in the ureter is improved, which may result in improved accuracy and reliability in the positioning of the ureteral catheter in the ureter, in particular during percutaneous delivery of the ureteral catheter.

The term to deliver fluid contrast agent near an end of the ureteral catheter means that the catheter system is configured to dispense fluid contrast agent from the catheter system into the environment of the catheter system near the respective end of the ureteral catheter. This contrast agent can be used to make the actual location of the respective end of the ureteral catheter in the patient's body better visible in an imaging catheter system susceptible for the respective fluid contrast agent.

The fluid contrast agent may be any contrast agent suitable to be used in a method of delivery of ureteral catheters. Such contrast agents are known in the art.

In an embodiment, the catheter system is, in the assembled state, configured to deliver, when desired, fluid contrast agent near a distal end of the ureteral catheter and to deliver, when desired, fluid contrast agent near a proximal end of the ureteral catheter.

By selective delivery of contrast fluid agent near one or both ends of the ureteral catheter the visibility of the ureteral catheter during insertion in the ureter may be further improved.

Since this embodiment of the catheter system makes it possible to dispense fluid contrast agent near both ends of the ureteral catheter, the catheter system may be suitable to be used in percutaneous delivery as well as cystoscopical delivery of the ureteral catheter.

This obviates the need of providing at least two different catheter systems for delivery of a ureteral catheter in a percutaneous method and for delivery of a ureteral catheter in a cystocopical method.

It is remarked that, in some embodiments, the presence of the guide wire in the guide wire lumen and the second guide wire lumen, in particular in the transition region between the proximal end of the guide wire lumen and the distal end of the second guide wire lumen may be required to selectively deliver fluid contrast agent near a distal end of the ureteral catheter and/or near a proximal end of the ureteral catheter.

In an embodiment, the catheter system comprises a first contrast agent channel to deliver fluid contrast agent near the distal end of the ureteral catheter and a second contrast agent channel near the proximal end of the ureteral catheter, wherein the first contrast agent channel and the second contrast agent channel are separate channels.

By providing separate channels to deliver fluid contrast agent near the distal end and near the proximal end of the ureter catheter, the contrast agent can selectively be dispensed by either one of the ends of the ureter catheter without the need of a valve or other control element to control the flow of contrast agent within the pusher catheter and/or the ureteral catheter.

The separate contrast agent channels may for example be formed by one or more contrast agent lumina, one running through the pusher catheter and ureteral catheter to eject contrast agent near the distal end of the ureteral catheter, and one running through the pusher catheter and possibly a part of the ureteral catheter to eject contrast agent near the proximal end of the ureteral catheter. The contrast agent lumina may be formed by lumina provided only for transport of contrast agent or lumina also having another function, such as a guide wire lumen.

In an embodiment, the ureteral catheter comprises a guide wire lumen and an auxiliary lumen, both extending from a proximal end of the ureteral catheter to a distal end of the ureteral catheter, and the pusher catheter comprises a second guide wire lumen and a second auxiliary lumen, both extending from a proximal end of the pusher catheter to a distal end of the pusher catheter, wherein, in the assembled state, a combination of the auxiliary lumen and one of the second auxiliary lumen and the second guide wire lumen forms a first contrast agent channel to deliver fluid contrast agent near the distal end of the ureteral catheter, and wherein the other of the second guide wire lumen and the second auxiliary lumen forms a second contrast agent channel to deliver fluid contrast agent near the proximal end of the ureteral catheter.

In a first embodiment, the first contrast agent channel to deliver fluid contrast agent near the distal end of the ureteral catheter may be formed by the combination of the auxiliary lumen and the second auxiliary lumen. The second contrast agent channel to deliver fluid contrast agent near the proximal end of the ureteral catheter may be formed by the second guide wire lumen. In an alternative embodiment, the second contrast agent channel may also be formed by a third auxiliary lumen in the pusher catheter.

In a second embodiment, the first contrast agent channel to deliver fluid contrast agent near the distal end of the ureteral catheter may be formed by the combination of the auxiliary lumen and the second guide wire lumen. And, the second contrast agent channel to deliver fluid contrast agent near the proximal end of the ureteral catheter may be formed by the second auxiliary lumen. In this second embodiment, the contrast agent should be guided at or near the transition from the pusher catheter to the ureteral catheter from the second guide wire lumen in the pusher catheter to the auxiliary lumen in the ureteral catheter.

A cross slot in the proximal end surface of the ureteral catheter and/or the distal end surface of the pusher catheter may for example provide such fluid connection between the second guide wire lumen in the pusher catheter and the auxiliary lumen in the ureteral catheter. Any other fluid connection between the second guide wire lumen in the pusher catheter and the auxiliary lumen in the ureteral catheter to create the first contrast agent channel may also be applied.

In an alternative embodiment, the part of the first contrast agent channel in the pusher catheter may also be formed by a third auxiliary lumen in the pusher catheter.

In an embodiment, the catheter system comprises a guide wire, and an inner diameter of at least a proximal part of the guide wire lumen is substantially the same or slightly larger than the outer diameter of the guide wire to provide a contrast agent seal between the guide wire lumen and the second guide wire lumen without obstructing relative movement of the ureteral catheter and the guide wire, when arranged in the guide wire lumen.

In the first and second embodiment, the diameter of the second guide wire lumen may be larger than the diameter of the guide wire to make the transport of contrast agent through the second guide wire lumen possible when a guide wire is located in the second guide wire lumen.

However, the entrance of fluid contrast agent in the guide wire lumen may be undesirable as the guide wire lumen may have over its length openings to the outside which openings may prevent that the contrast agent is ejected near a proximal or distal end of the ureteral catheter.

To avoid or substantially reduce the possibility that contrast agent enters the guide wire lumen of the ureteral catheter, the inner diameter of at least a proximal part of the guide wire lumen of the ureteral catheter is selected to substantially correspond to or to be slightly larger than the diameter of the guide wire without obstructing relative movement of ureteral catheter with respect to the guide wire lumen. In this way a contrast agent seal is created in a proximal part of the ureteral catheter.

The inner diameter of the guide wire lumen in a widened connector element, also known as overmould, provided to connect a proximal end of the ureteral catheter to a distal end of the pusher catheter, may for example be selected to substantially correspond to or to be slightly larger than the diameter of the guide wire to provide a sliding seal between the guide wire and the guide wire lumen.

Any other sealing device, such as a sealing ring, to avoid or substantially reduce the possibility that contrast agent enters the guide wire lumen of the ureteral catheter from a contrast agent lumen of the pusher catheter, in particular the second guide wire lumen, may also be applied.

It is remarked that this difference in diameter of at least the proximal part of the guide wire lumen and the second guide wire lumen may also be used to push with an elongate pusher element, for example a stylet, having a diameter larger than the inner diameter of the guide wire lumen, but smaller than the diameter of the second guide wire lumen, the ureteral catheter away from the pusher catheter to release the ureteral catheter and therewith disconnecting the connection of the connection device.

When in an embodiment, both the auxiliary lumen and the second auxiliary lumen are configured to transport fluid contrast agent through the catheter system, the auxiliary lumen and the second auxiliary lumen may also be indicated as contrast agent lumen and second contrast agent lumen.

In an embodiment, the other of the second guide wire lumen and the second auxiliary lumen comprises a contrast agent outlet port near a distal end of the pusher catheter.

In the first embodiment, the contrast agent outlet port may be formed by a side port of the second guide wire lumen, connecting the second guide wire lumen with an outer surface of the pusher catheter at or near the distal end of the pusher catheter. By ejecting contrast fluid from such side port, contrast fluid can be dispensed near the proximal end of the ureteral catheter.

In the second embodiment, the contrast agent outlet port may be formed by an end or side opening of the second auxiliary lumen arranged in an outer surface of the pusher catheter at or near the distal end of the pusher catheter. In this embodiment, contrast fluid ejected from such end opening of the second auxiliary lumen, will also be dispensed near the proximal end of the ureteral catheter.

In an embodiment, the pusher catheter comprises a side inlet port configured to introduce fluid contrast agent into the second auxiliary lumen. A side inlet port may be provided to introduce contrast agent into the second auxiliary lumen. The side inlet port may also be provided to introduce contrast agent into the second guide wire lumen. In yet an alternative embodiment, the pusher catheter may comprise two side inlet ports; one for to introduce contrast agent into the second auxiliary lumen and a second to introduce contrast agent into the second guide wire lumen.

In an embodiment, the catheter system comprises a Y-connection device connected on the proximal end of the pusher catheter, wherein the Y-connection device comprises a second side inlet port configured to introduce fluid contrast agent into the second guide wire lumen. This second side inlet port may also be used to introduce contrast agent into the second auxiliary lumen. Any other device to introduce contrast agent into one of the second guide wire lumen and second auxiliary lumen may also be applied.

In an embodiment, the connection device comprises a mini tube arranged, in the assembled state, in a proximal end of the auxiliary lumen and a distal end of the second auxiliary lumen, therewith providing a fluid connection between the auxiliary lumen and the second auxiliary lumen and forming the first contrast agent channel. Such mini tube can provide a connection to hold the pusher catheter as long as the ureteral catheter is not to be released from the pusher catheter, as well as a fluid connection between the auxiliary lumen and the second auxiliary lumen to form the first contrast agent channel. The mini tube is a tube with a relative small diameter that is, in this arrangement selected to fit in the respective lumen or lumina. The mini tube has an outer diameter that substantially corresponds to an inner diameter of at least one, preferably both, of the lumina in which it is placed to provide a substantially sealing fit between between the outer surface of the mini tube and the inner surface of the respective lumen. One end of the mini tube may be fixed to the proximal end of the auxiliary lumen or the distal end of the second auxiliary lumen.

In an embodiment, the ureteral catheter is a double J catheter, such as for example disclosed in US application number US 2007/0276466 or a ureteral balloon catheter, as for example disclosed in U.S. Pat. No. 6,066,113.

In an embodiment, the catheter system comprises a valve system to deliver fluid contrast agent from a single contrast agent source connected to a single contrast agent inlet port of the catheter system selectively near a distal end of the ureteral catheter and/or near a proximal end of the ureteral catheter. Instead of two separate contrast agent channels, from contrast agent inlet to contrast agent outlet, the catheter system may also comprise a valve system to eject contrast agent introduced from a single contrast agent inlet selectively near a distal end of the ureteral catheter and/or near a proximal end of the ureteral catheter.

For example, at the distal end of the second auxiliary lumen a valve device may be provided to guide contrast agent to the auxiliary lumen of the ureteral catheter to eject contrast agent near a distal end of the ureteral catheter and/or to a side port of the second auxiliary lumen to eject contrast agent near a proximal end of the ureteral catheter.

In an embodiment, the pusher catheter comprises a fluid contrast agent outlet port near a distal end of the pusher catheter to deliver fluid contrast agent near the proximal end of the ureteral catheter, wherein the fluid contrast agent outlet port is in fluid communication with a guide wire lumen or an auxiliary lumen of the pusher catheter. The guide wire lumen or auxiliary lumen may form a fluid contrast agent channel from a proximal end of the pusher catheter to the fluid contrast agent outlet port.

In an embodiment, the ureteral catheter comprises a guide wire lumen and an auxiliary lumen, wherein the guide wire lumen comprises side drainage openings between at least a proximal opening and a distal opening of the guide wire lumen, and wherein the auxiliary lumen is a closed channel between a proximal opening and a distal opening of the auxiliary lumen to transport fluid contrast agent from the proximal opening to the distal opening of the auxiliary lumen.

Another aspect of the invention relates to a ureteral catheter comprising a guide wire lumen and an auxiliary lumen, wherein the guide wire lumen and the auxiliary lumen each run from a proximal opening at a proximal end of the ureteral catheter to a distal opening at a distal end of the ureteral catheter, wherein the guide wire lumen comprises a plurality of side drainage openings to an outer surface of the ureteral catheter between the proximal opening and the distal opening of the guide wire lumen, and wherein the auxiliary lumen is a closed channel between the proximal opening and the distal opening of the auxiliary lumen to transport fluid contrast agent from the proximal opening to the distal opening of the auxiliary lumen.

This aspect of the invention also provides a catheter system for delivery of a ureteral catheter in a ureter, comprising:
  a ureteral catheter,
  a pusher catheter to deliver the ureteral catheter at a desired location, a connection device, to connect, in an assembled state a distal end of the pusher catheter to a proximal end of the ureteral catheter.

wherein, in the assembled state, the catheter system is configured to deliver, when desired, fluid contrast agent near a distal end of the ureteral catheter.

The invention further relates to the use of a catheter system for the treatment of a diseased, in particular stenosed ureter of a patient, and to a method for delivery of a ureteral catheter in a patient's ureter, wherein the use or method comprises the steps of:

inserting, in assembled state, the combination of ureter catheter and pusher catheter into the patient to place the ureter catheter in the ureter to be treated;

releasing at a desired location the ureteral catheter from the pusher catheter; and retracting the pusher catheter from of the patient, comprising the step of ejecting fluid contrast agent near the distal end and/or near the proximal end of the ureteral catheter during the step of inserting and or releasing.

BRIEF DESCRIPTION OF THE DRAWINGS

Further characteristics and advantages of the invention will now be elucidated by a description of embodiments of the invention, with reference to the accompanying drawings, in which:

FIG. 1 shows a perspective view of a ureteral catheter according to an embodiment of the invention;

FIG. 2a shows a cross section A-A of the ureteral catheter of FIG. 1;

FIG. 2b shows a cross section B-B of the ureteral catheter of FIG. 1;

FIG. 3 shows a side view of a pusher catheter according to an embodiment of the invention;

FIG. 4 shows a cross section C-C of the pusher catheter of FIG. 3;

FIG. 5 shows a side view of a first embodiment of a catheter system according to the invention;

FIG. 5a shows a longitudinal cross-section of a part of the catheter system of FIG. 5;

FIG. 6 shows a side view of a second embodiment of a catheter system according to the invention; and FIG. 6a shows a longitudinal cross-section of a part of the catheter system of FIG. 6.

DETAILED DESCRIPTION OF THE INVENTION

FIG. 1 shows a perspective view of a ureteral catheter, in particular a double J catheter, generally indicated by reference numeral 1. The ureteral catheter 1 comprises an elongate body 2 having a proximal end 3 and a distal end 4. The proximal end 3 comprises a widened connector element 5, also referred to as overmould, to connect the ureteral catheter 1 to a pusher catheter. This connector element 5 may be made of relative hard material compared to the further parts of the ureteral catheter to make a more reliable connection to the pusher catheter possible.

The ureteral catheter 1 is configured to be placed in the ureter to be treated typically to restore and/or ensure patency of the ureter. After positioning of the ureteral catheter 1 in the ureter, the ureteral catheter 1 will extend from the bladder to the pyelum.

The proximal end 3 and the distal end 4 are formed as a pigtail or coil to make sure that the respective ends remains properly positioned in the bladder and pyelum in which it is placed. The proximal end 3 and the distal end 4 of the ureteral catheter are suitable to be placed in both the pyelum and the bladder, dependent on the direction of introduction into the ureter.

FIG. 2a shows a cross-section A-A of the ureteral catheter 1 in the elongate middle part thereof. The ureteral catheter 1 comprises a guide wire lumen 6 and a contrast agent lumen 7. Both the guide wire lumen 6 and the contrast agent lumen 7 run from the proximal end 3 of the ureteral catheter 1 to the distal end 4 of the ureteral catheter 1. At least over the relative straight middle part of the ureteral catheter 1, the contrast agent lumen 7 is a closed channel, i.e. fluid tight to the outer surface of the ureteral catheter 1 such that from a proximal opening at the proximal end of the ureteral catheter 1, contrast agent can be transported to a distal opening at the distal end of the ureteral catheter 1.

The guide wire lumen 6 may have a number of drainage openings 9 along the length of the guide wire lumen to promote fluid flow through the ureter after placement of the ureteral catheter. These drainage openings 9 may improve the drainage effect of the ureteral catheter 1.

At the proximal end 3 and the distal end 4, the guide wire lumen 6 and the contrast agent lumen 7 comprise one or more openings to the outer side of the ureteral catheter 1. The distal end 4 of the ureteral catheter 1 may be tapered, preferably towards a diameter slightly larger than the guide wire lumen 6. The distal end of the contrast agent lumen 7 may be formed by an elongate opening or a side opening, for example in the tapered distal end of the ureteral catheter. The elongate opening or the side opening part is preferably designed to avoid or minimize scraping thereof against an inner wall of the ureter or other part of the patient's body.

The guide wire lumen 6 is configured to receive a guide wire 10, indicated by dashed lines in FIG. 2. The guide wire 10 can be used to guide the ureteral catheter 1 to the desired location in the ureter.

The diameter of the guide wire lumen 6 is substantially larger than the diameter of the guide wire 10 to obtain a space between the inner surface of the guide wire lumen 6 and the outer surface of the guide wire 10. This space can be used for the transport of fluid through the ureteral catheter when the guide wire 10 is still arranged in the guide wire lumen 6.

The contrast agent lumen 7 is configured to transport contrast fluid from the proximal end 3 to the distal end 4 to eject the contrast fluid at or near the distal end 4 of the ureteral catheter 1 during insertion and positioning of the ureteral catheter 1 in the ureter. In this embodiment, the diameter of the contrast agent lumen 7 is smaller than the diameter of the guide wire lumen 6.

FIG. 2b shows a cross-section B-B of the ureteral catheter 1 at the connector element 5. Also in this cross-section the guide wire lumen 6 and the contrast agent lumen 7 running over the length of the ureteral catheter 1 are shown.

In the connector element 5, the diameter of the guide wire lumen 6 is substantially the same as or slightly larger than the diameter of the guide wire 10 to obtain a relative tight fit between guide wire lumen 6 and guide wire, however without obstructing movement of the guide wire 10 with respect to the ureteral catheter 1. This tight fit is useful to make release of the ureteral catheter 1 from the pusher catheter 20 possible as well as to avoid that contrast agent may enter the guide wire lumen 6 of the ureteral catheter 1, as will be discussed hereinafter.

FIG. 3 shows an embodiment of a pusher catheter 20. The pusher catheter 20 comprises an elongate pusher catheter body 21 and a Y shaped part 22. The pusher catheter 20 has a distal end 23. At the distal end 23 a distally extending cover tube 24 is provided to receive the connector element 5 of the ureteral catheter 1. By arranging the connector element 5 in the cover tube 24, the proximal end 3 of the ureteral catheter 1 may be connected to the distal end 23 of the pusher catheter 20. Additionally, or as an alternative, other connection means may be provided to couple the ureteral catheter 1 and the pusher catheter 20.

FIG. 4 shows a cross section C-C of the pusher catheter 20. The pusher catheter 20 comprises a second guide wire lumen 25 and a second contrast agent lumen 26. Both the second guide wire lumen 25 and the second contrast agent lumen 26 run from a proximal end of the pusher catheter 20 to the distal end 23 of the pusher catheter 20. At the proximal end of the pusher catheter 20, the second guide wire lumen 25 is fluidly connected to a main port 27 of the pusher catheter 20 and the second contrast agent lumen 26 is connected to a side port 28 of the pusher catheter 20.

It is remarked that in the shown embodiment of FIGS. 3 and 4, the pusher catheter 20 only comprises one guide wire lumen 25 and one contrast agent lumen 26. The term 'second' is used to distinguish the guide wire lumen 25 and the contrast agent lumen 26 of the pusher catheter 20 from the guide wire lumen 6 and the contrast agent lumen 7 of the pusher catheter 20.

In the guide wire lumen 25 a guide wire 10 is shown, having the same diameter as the guide wire 10 in FIG. 2. The diameter of the second guide wire lumen 25 is larger than the diameter of the guide wire lumen 6. The space 29 in the second guide wire lumen 25 not occupied by the guide wire 10 may be used to transport contrast fluid from the main port 27 to the distal end 23 of the pusher catheter 20.

FIG. 5 shows a catheter system for delivery of a ureteral catheter in a ureter. The catheter system comprises the ureteral catheter 1, as shown in FIG. 1, and a pusher catheter 20, as shown in FIG. 3. On the main port 27 of the pusher catheter 20 a further Y-connector element 40 is mounted. The Y-connector element 40 comprises guide wire port 41 and a contrast agent side port 42. The guide wire port 41 and the contrast agent side port 42 are connected to the same central lumen in the Y-connector element 40 running from the guide wire port 41 to the distal end 43 of the Y-connector element 40, which is mounted on the main port 27 of the pusher catheter 20.

The diameter of the central lumen is selected to be larger than the guide wire 10, for example similar to the diameter of the guide wire lumen 25 of the pusher catheter 20, so that contrast agent can be transported towards the distal end 43 when a guide wire 10 is positioned in the central lumen.

The guide wire port 41 is configured to receive a guide wire 10 in a sealing way so that it is avoided that contrast agent introduced through the contrast agent side port 42 will leave the Y-connector element 40 via the guide wire port 41.

In the assembled state of the catheter system, as shown in FIG. 5, guide wire lumen 6, the second guide wire lumen 25 and the central lumen are aligned so that the guide wire 10 runs from the proximal end of the catheter system at guide wire port 41 to the distal end of the catheter system to leave the ureteral catheter 1 at a guide wire opening at the distal end 4 of the ureteral catheter 1. As a result, of the presence of the guide wire 10 in the guide wire lumen 6 of the ureteral catheter 1, the coiled ends of the ureteral catheter 1, are straightened. When the guide wire 10 is removed from the guide wire lumen 6 the proximal end 3 and the distal end 4 will return to the coiled shape.

The side port 28 of the pusher catheter 20 and the contrast agent side port 42 of the Y-connector element 40 provide the possibility to introduce contrast agent at two locations of the catheter system. Each of the side port 28 and the contrast agent side port 42 is connected to a separate contrast agent channel, one configured to eject fluid contrast agent near the distal end 4 of the ureteral catheter 1 and one configured to eject fluid contrast agent near the proximal end 3 of the ureteral catheter 1.

By delivering contrast agent at both the proximal end 3 and the distal end 4 during insertion and positioning of the ureteral catheter 1 in the ureter, the actual location of the ureteral catheter 1 can be made more visible in an imaging catheter system susceptible for the contrast agent. Furthermore, the possibility of ejecting or dispensing contrast agent near a selected one and/or both ends of the ureteral catheter 1, makes the catheter system suitable to be used in both percutaneous delivery, from kidney to bladder, and cystoscopical delivery, from bladder to kidney, of the ureteral catheter 1 in the ureter.

The advantage of separate contrast agent channels is that contrast agent can be ejected selectively near one or both of the proximal end 3 and the distal end 4 of the ureteral catheter 1. There is no need to provide valve elements or other fluid flow control elements to guide the flow of fluid contrast agent to a selected one of the proximal end 3 and the distal end 4.

In the transition of the pusher catheter 20 to the ureteral catheter 1, the contrast agent flows can be created differently.

FIG. 5a shows a first possibility to create two separate contrast agent channels. In the embodiment of FIG. 5a a connection mini tube 30 is provided in a distal end opening of the second contrast agent lumen 26 and in a proximal end opening of the contrast agent lumen 7. One end of the mini tube 30 may be fixed to the pusher catheter 20, and the other end may be slidable, with some friction, with respect to the proximal end opening of the contrast agent lumen 7.

The connection mini tube 30 provides a further connection between ureteral catheter 1 and pusher catheter 20, and forms a fluid passage from the second contrast agent lumen 26 to the contrast agent lumen 7. As a result, a first contrast agent channel is formed running from the side port 28 to a distal end 4 of the ureteral catheter 1.

Near a distal end 23 of the pusher catheter 20 a contrast agent outlet port 31 is formed providing a fluid connection between the second guide wire lumen 25 and the outer surface of the pusher catheter body 21. As a result, the second guide wire lumen 25 forms a second contrast agent channel from the contrast agent side port 42 to the contrast agent outlet port 31.

Since the contrast agent outlet port 31 is arranged, in the assembled state, close to the proximal end 3 of the ureteral catheter 1, any contrast agent ejected from the contrast agent outlet port 31 will be ejected near the proximal end 3 of the ureteral catheter 1.

As discussed above, the diameter of the guide wire lumen 6 in the connector element 5 is smaller than the diameter of the, in assembled state, axially aligned second guide wire lumen 25. Since the diameter of the guide wire lumen 6 is substantially the same as or only slightly larger than the diameter of the guide wire 10, no or little contrast agent will continue to flow from the second guide wire lumen 25 into the guide wire lumen 6 towards the distal end 3 of the ureteral catheter 1. As a result, substantially all contrast agent introduced at contrast agent side port 42 will be ejected from the pusher catheter 20 at the contrast agent outlet port 31.

It is remarked that this difference in diameter may also be used to release the ureteral catheter 1 from the pusher catheter 20 by introducing a pusher element, for example a push rod, also called stylet, into the second guide wire lumen 25. When this pusher element has a smaller diameter than the second guide wire lumen 25, but a larger diameter than the guide wire lumen 6 in the connector element 5, the pusher element cannot, when advanced in the second guide wire lumen 25 enter the guide wire lumen 6, and will abut against the proximal end surface of the ureteral catheter 1. By exerting a force on the pusher element positioned against the proximal end surface of the ureteral catheter 1, the ureteral catheter 1 can be pushed away from the pusher catheter 20 and released when the connector element 5 is completely pushed out of the cover tube 14.

It is further remarked that for this release of the ureteral catheter 1 from the pusher catheter also other shapes or devices may be used, such as an oval cross-section of the guide wire lumen at the connector element 5 having a minimal diameter smaller than the diameter of the pusher element, or the provision of one or more stop elements such as extensions extending into the guide wire lumen at the proximal end thereof to prevent entrance of the pusher element into the guide wire lumen 6 of the ureteral catheter 1.

FIGS. 6 and 6a show a second embodiment of a catheter system according to the invention. The same parts or parts having substantially the same function are indicated by the same reference numerals.

The catheter system comprises a ureteral catheter 1, a pusher catheter 20, and a Y-connector element 40. The catheter system of FIGS. 6 and 6a is, in the assembled state, also configured to deliver, when desired, fluid contrast agent near a distal end of the ureteral catheter and, when desired, near a proximal end of the ureteral catheter.

Similar to the embodiment of FIG. 5, the catheter system is configured to provide a first contrast agent flow from the side port 28 via the second contrast agent lumen 26 towards the distal end 23 of the pusher catheter 20, and a second contrast agent flow from the contrast agent side port 42 via the second guide wire lumen 25 towards the distal end 23 of the pusher catheter 20.

FIG. 6a shows a cross section of the transition from the distal end 23 of the pusher catheter 20 to the proximal end 3 of the ureteral catheter 1.

In this embodiment a cross slot 8 is provided in the proximal end 3 of the ureteral catheter 1. The cross slot 8 provides a fluid connection between the second guide wire lumen 25 and the contrast agent lumen 7. The second contrast agent lumen 26 is not in fluid connection with the contrast agent lumen 7.

As a result, a first separate contrast agent channel is formed from the contrast agent side port 42 via the second guide wire lumen 25, cross slot 8 and contrast agent lumen 7 to the distal end 4 of the ureteral catheter 1. This first contrast agent channel is thus suitable to dispense contrast agent near the distal end 4 of the ureteral catheter 1. Again, no or little contrast agent will enter the guide wire lumen 6 due to the relative close fit between the proximal part of the guide wire lumen 6 and the guide wire 10 in the connector element 5.

A second contrast agent channel is formed by the second contrast agent lumen 26 running from the side port 28 to the distal end 23 of the pusher catheter 20. The axial end of this second contrast agent lumen 26 is closed, but a contrast agent outlet port 31 provides a fluid connection between the second contrast agent lumen 26 and an outer surface of the pusher catheter 20, so that contrast agent can be ejected from the contrast agent outlet port 31 at the distal end 23 of the pusher catheter, and therefore, in the assembled state, near the proximal end 3 of the ureteral catheter 1.

The different parts of the catheter system may be produced by any suitable method and from any suitable material known in the art. The ureteral catheter and the pusher catheter are preferably made from biocompatible plastics materials. The guide wire is preferably made of a biocompatible metal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A catheter system for delivery of a ureteral catheter in a ureter, comprising:
   a ureteral catheter,
   a pusher catheter to deliver the ureteral catheter at a desired location, and a releasable connection device, to connect, in an assembled state a distal end of the pusher catheter to a proximal end of the ureteral catheter,
   wherein the catheter system comprises a first contrast agent channel to deliver, when desired, fluid contrast agent near a distal end of the ureteral catheter and a second contrast agent channel to deliver, when desired, fluid contrast agent near the proximal end of the ureteral catheter,
   wherein the first contrast agent channel and the second contrast agent channel are separate channels, and
   wherein the first contrast agent channel and the second contrast agent channel run at least partially through the pusher catheter.

2. The catheter system of claim 1,
   wherein the ureteral catheter comprises a guide wire lumen and an auxiliary lumen, both extending from a proximal end of the ureteral catheter to a distal end of the ureteral catheter,
   wherein the pusher catheter comprises a second guide wire lumen and a second auxiliary lumen, both extending from a proximal end of the pusher catheter to a distal end of the pusher catheter,
   wherein, in the assembled state, a combination of the auxiliary lumen and one of the second auxiliary lumen and the second guide wire lumen forms the first contrast agent channel to deliver fluid contrast agent near the distal end of the ureteral catheter, and
   wherein the other of the second guide wire lumen and the second auxiliary lumen forms the second contrast agent channel to deliver fluid contrast agent near the proximal end of the ureteral catheter.

3. The catheter system of claim 2, wherein the other of the second guide wire lumen and the second auxiliary lumen comprises a fluid contrast agent outlet port near a distal end of the pusher catheter.

4. The catheter system of claim 2, wherein the pusher catheter comprises a side inlet port configured to introduce fluid contrast agent into the second auxiliary lumen.

5. The catheter system of claim 2, wherein the connection device comprises a mini tube arranged, in the assembled state, in a proximal end of the auxiliary lumen and a distal end of the second auxiliary lumen, therewith providing a fluid connection between the auxiliary lumen and the second auxiliary lumen and forming the first contrast agent channel.

6. The catheter system of claim 2, wherein a fluid connection between the second guide wire lumen in the pusher catheter and the auxiliary lumen in the ureteral catheter to form the first contrast agent channel is formed by a cross slot in a proximal end surface of the ureteral catheter and/or in a distal end surface of the pusher catheter.

7. The catheter system of claim 2, wherein the catheter system comprises a guide wire, and wherein an inner diameter of at least a proximal part of the guide wire lumen is substantially the same or slightly larger than the outer diameter of the guide wire to provide a contrast agent seal between the guide wire lumen and the second guide wire lumen without obstructing relative movement of the ureteral catheter and the guide wire, when arranged in the guide wire lumen.

8. The catheter system of claim 2, wherein the catheter system comprises a guide wire, and a sealing device to provide a contrast agent seal between the guide wire lumen and the second guide wire lumen without obstructing relative movement of the ureteral catheter and the guide wire, when arranged in the guide wire lumen.

9. The catheter system of claim 2, wherein the catheter system comprises a Y-connection device connected on the proximal end of the pusher catheter, wherein the Y-connection device comprises a second side inlet port configured to introduce fluid contrast agent into the second guide wire lumen.

10. The catheter system of claim 1, wherein the catheter system comprises a valve system to deliver fluid contrast agent from a single contrast agent source connected to a single contrast agent inlet port of the catheter system selectively near a distal end of the ureteral catheter and/or near a proximal end of the ureteral catheter.

11. The catheter system of claim 1, wherein the pusher catheter comprises a fluid contrast agent outlet port near a distal end of the pusher catheter to deliver fluid contrast agent near the proximal end of the ureteral catheter, wherein the fluid contrast agent outlet port is in fluid communication with a guide wire lumen or an auxiliary lumen of the pusher catheter.

12. The catheter system of claim 1, wherein the ureteral catheter comprises a guide wire lumen and an auxiliary lumen, wherein the guide wire lumen comprises side drainage openings between at least a proximal opening and a distal opening of the guide wire lumen, and wherein the auxiliary lumen is a closed channel between a proximal opening and a distal opening of the auxiliary lumen to transport fluid contrast agent from the proximal opening to the distal opening of the auxiliary lumen.

13. The catheter system of claim 1, wherein the ureteral catheter is a double J catheter or a ureteral balloon catheter.

14. Use of a catheter system according to claim 1 for the treatment of a diseased ureter of a patient, comprising:
  inserting, in assembled state, the combination of ureter catheter and pusher catheter into the patient to place the ureter catheter in the ureter to be treated;
  releasing at a desired location the ureteral catheter from the pusher catheter;
  retracting the pusher catheter from of the patient, and
  ejecting fluid contrast agent near the distal end and/or near the proximal end of the ureteral catheter during the step of inserting and/or releasing.

* * * * *